US008535329B2

(12) United States Patent
Sarin et al.

(10) Patent No.: US 8,535,329 B2
(45) Date of Patent: Sep. 17, 2013

(54) TRACKING TOOLS AND METHOD FOR COMPUTER-ASSISTED SHOULDER REPLACEMENT SURGERY

(75) Inventors: Vineet Kumar Sarin, Thousand Oaks, CA (US); William Ralph Pratt, Newbury Park, CA (US); Kyle Craig Pilgeram, Oxnard, CA (US); Richard Lee Kendall, Oak View, CA (US)

(73) Assignee: Kinamed, Inc., Camarillo, CA (US)

( * ) Notice: Subject to any disclaimer, the term of this patent is extended or adjusted under 35 U.S.C. 154(b) by 1605 days.

(21) Appl. No.: 10/975,211

(22) Filed: Oct. 29, 2004

(65) Prior Publication Data

US 2006/0100638 A1    May 11, 2006

(51) Int. Cl.
*A61B 17/56* (2006.01)

(52) U.S. Cl.
USPC .......................................... 606/102; 606/130

(58) Field of Classification Search
USPC ................. 606/130, 54, 56, 60, 87, 96, 151, 606/906, 86 R, 102, 248, 902; 600/407, 600/414, 426, 424; 248/200, 220.1, 205.1, 248/223.41, 224.51, 224.61, 224.7, 225.11; 42/124; 269/45; 29/257; 40/605, 611.05, 40/661.02, 661.03; 232/39; 33/263, 265; 124/87
See application file for complete search history.

(56) References Cited

U.S. PATENT DOCUMENTS

| 1,799,944 | A | * | 4/1931 | Beardsley | 248/220.1 |
| 3,593,709 | A | * | 7/1971 | Halloran | 606/283 |
| 3,614,950 | A | * | 10/1971 | Rabey | 600/587 |
| 3,814,089 | A | * | 6/1974 | Deyerle | 606/98 |
| 4,920,958 | A | * | 5/1990 | Walt et al. | 606/96 |
| 5,364,402 | A | * | 11/1994 | Mumme et al. | 606/88 |
| 5,549,612 | A | * | 8/1996 | Yapp et al. | 606/293 |
| 6,351,659 | B1 | * | 2/2002 | Vilsmeier | 600/407 |
| 6,450,978 | B1 | * | 9/2002 | Brosseau et al. | 600/595 |
| 6,474,901 | B1 | * | 11/2002 | Thurston | 403/381 |
| 6,491,699 | B1 | * | 12/2002 | Henderson et al. | 606/130 |
| 6,551,325 | B2 | * | 4/2003 | Neubauer et al. | 606/88 |
| 6,711,431 | B2 | | 3/2004 | Sarin et al. | 600/426 |
| 2002/0133175 | A1 | * | 9/2002 | Carson | 606/130 |
| 2003/0225329 | A1 | * | 12/2003 | Rossner et al. | 600/424 |
| 2004/0039396 | A1 | * | 2/2004 | Couture et al. | 606/87 |
| 2004/0097952 | A1 | * | 5/2004 | Sarin et al. | 606/102 |

(Continued)

FOREIGN PATENT DOCUMENTS

WO    WO 2004014219 A2    2/2004

OTHER PUBLICATIONS

Bicknell, et al.; "Computer-Assisted Shoulder Hemiarthroplasty for Fractures of the Proximal Humerus: an in Vitro Comparison With Traditional Methods"; Fourth Annual Meeting of the International Computer-Assisted Orthopaedic Society; Chicago, 2004; pp. 131-132.

(Continued)

*Primary Examiner* — Kevin T Truong
*Assistant Examiner* — Christian Sevilla
(74) *Attorney, Agent, or Firm* — Koppel, Patrick, Heybl & Philpott

(57) ABSTRACT

The invention includes a method for tracking the human scapula during shoulder surgery, by a trackable device fixed to the coracoid process of the scapula. A device of the invention allows a trackable target to be fixed to the coracoid process by bone screws and an anchor. In one embodiment, a releasable coupling is provided between the anchor and the trackable target.

14 Claims, 4 Drawing Sheets

(56) References Cited

U.S. PATENT DOCUMENTS

2004/0102792 A1* 5/2004 Sarin et al. .................... 606/151
2004/0172044 A1* 9/2004 Grimm et al. ................. 606/130
2005/0261697 A1* 11/2005 Canonaco et al. .............. 606/89

OTHER PUBLICATIONS

International Search Report and Written Opinion, dated Jun. 18, 2008; for International Application No. PCT/US2005/038712.

* cited by examiner

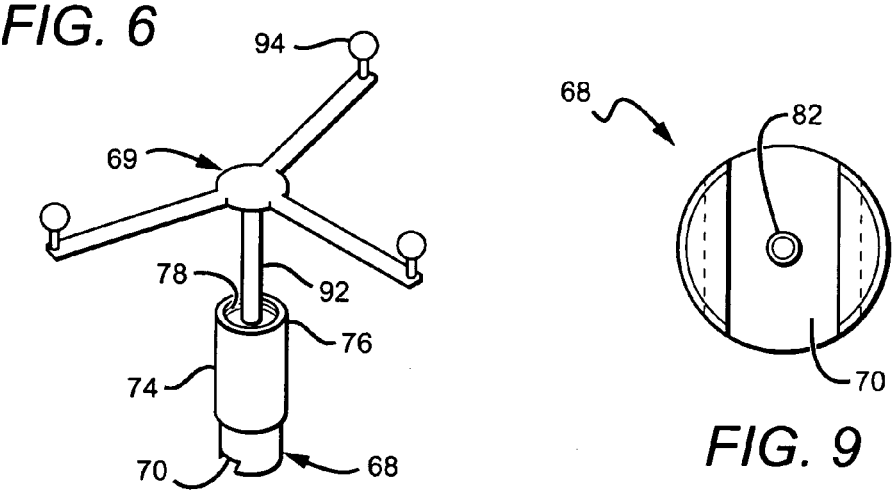
FIG. 6
FIG. 9
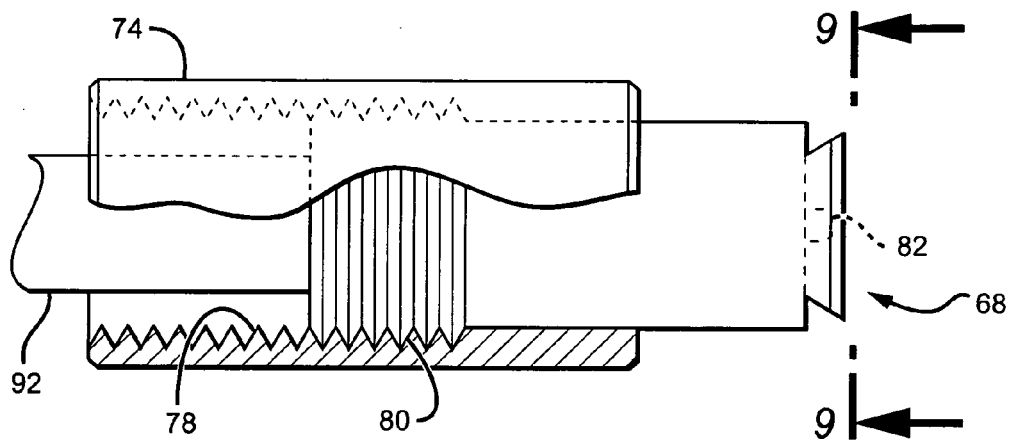
FIG. 7
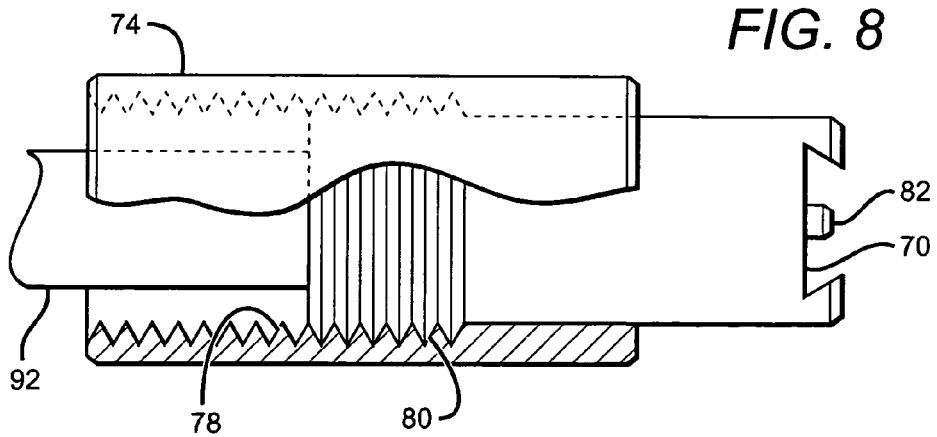
FIG. 8

TRACKING TOOLS AND METHOD FOR COMPUTER-ASSISTED SHOULDER REPLACEMENT SURGERY

BACKGROUND OF THE INVENTION

1. Field of the Invention

This invention relates to computer assisted surgery generally and more specifically to orthopedic joint replacement surgery of the shoulder.

2. Description of the Related Art

Computer-aided tracking technology has been developed and successfully used for many types of surgical intervention. In orthopedic surgery, computer-aided tracking technology (i.e. navigation) has been developed for hip, knee, and spine surgery. One system for computer assisted hip navigation is described in U.S. Pat. No. 6,711,431 to Sarin, et al. (March 2004). Other reports of computer assisted surgical navigation are available in the medical and patent literature. Use of navigation technology in shoulder surgery is much more recent and less developed. One publication describes navigation in shoulder arthroplasty surgery, but that disclosure is limited to a method of orienting the humeral implant in treating shoulder fractures[1]. See Bicknell et al., "Computer-assisted Shoulder Hemiarthroplasty for fractures of the Proximal Humerus: an in vitro Comparison with Traditional Methods," Fourth annual Meeting of the International Computer-Assisted Orthopaedic Society, (Chicago, 2004) pp. 131-132. Orientation of the glenoid component was not addressed in that publication.

FIG. 1 shows the skeletal structure of the human shoulder joint. This joint enables the Humerus 10 to pivot with respect to the Scapula 12. In total shoulder arthroplasty surgery, both the glenoid cavity 14 and humeral head 16 are replaced by prosthetic implants. The spatial orientation of these implants is a critical parameter that can determine surgical success and implant longevity. The glenoid component, in particular, must be properly oriented with respect to the scapula and to the humeral head in order to function correctly. One of the shoulder arthroplasty surgeon's primary intra-operative goals is achievement of correct glenoid component alignment and orientation.

Glenoid component orientation is defined in terms of two angular measurements: the inclination and version angles. Both angles are defined relative to planes of the scapula. Inclination is expressed in an anterior-posterior (front-to-back) projection of the scapula while version is expressed in an axillary (top-to-bottom) projection. Both inclination and version of the glenoid component are usually determined by the surgeon using manual instruments that prepare the native glenoid cavity for implantation. Typically, the surgeon uses visual cues and experience to determine the final orientation of the glenoid component. As in hip replacement surgery, such methods are not robust and frequently result in less than optimal orientations. The use of navigation in shoulder replacement surgery is expected to provide a significant clinical benefit, particularly due to improved orientation of the glenoid component.

Automated tracking devices and software have been developed which can assist in tracking and measuring individual bones in real time during surgery, as described in the Sarin patent referenced above and elsewhere. However, there is a need for specific devices and methods to apply such tracking techniques to shoulder replacement surgery.

SUMMARY OF THE INVENTION

According to one aspect, the present invention is an attachable surgical anchor, for attaching a trackable target in fixed relation to a human scapula during shoulder replacement surgery. The anchor includes a body having at least two bores for receiving shafts of bone screws, the bores arranged to direct the bone screws into a bone, thereby securing said body to the bone. The anchor also includes a coupling member, carried by the body and arranged to engage a complementary coupling member bearing a trackable target. The anchor body is suitable for mounting on the coracoid process of the human scapula.

The invention also includes a method for tracking the scapula by attaching a trackable target to the coracoid process, tracking the target, and inferring the position of the scapula based on the position and orientation of the coracoid process. In one embodiment, the method includes the further steps of detaching and reattaching the trackable target during surgery.

According to another aspect, the invention includes a trackable surgical target device, ountable on a scapula to track the scapula during a shoulder surgery. The device includes an anchor body with at least two bores for receiving the shafts of bone screws, arranged to direct the bone screws into a bone thereby securing the anchor to the bone. A trackable target is mounted on the body and may be integral with the body.

These and other features and advantages of the invention will be apparent to those skilled in the art from the following detailed description of preferred embodiments, taken together with the accompanying drawings, in which:

BRIEF DESCRIPTION OF THE DRAWINGS

FIG. 6 is perspective view of a trackable marker mounted on a coupling member, suitable for coupling to the anchor of FIG. 2;

FIG. 7 is a side elevation view of the coupling member in FIG. 6;

FIG. 8 is another side view of the coupling member of FIG. 7, rotated ninety degrees;

FIG. 9 is a plan view from below of the coupling member of FIGS. 7 and 8; and

DETAILED DESCRIPTION OF THE INVENTION

Because the trunk of a patient may move during surgery, and because the scapula may move relative to the other bones in the body, it is desirable to track the scapula in real-time during navigated shoulder replacement surgery. To facilitate such tracking, a trackable target is required to be mounted to the scapula.

Figure 1:
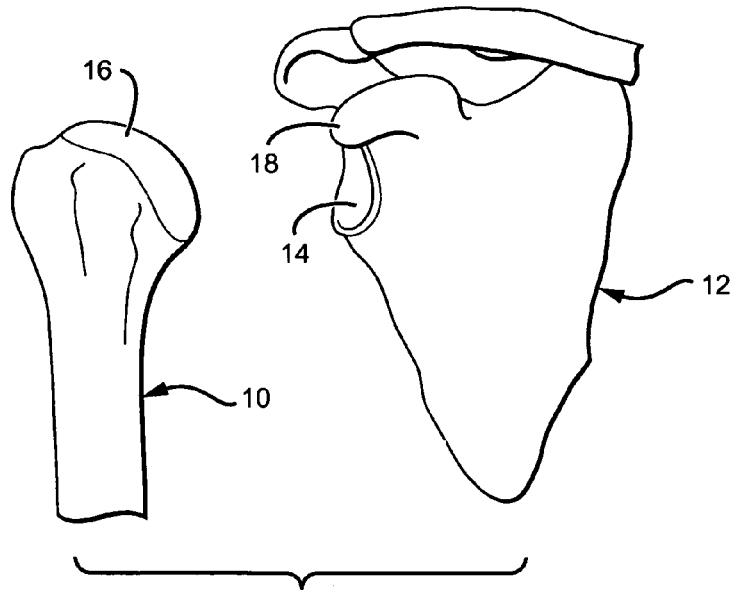
FIG. 1 is an exploded perspective view of a human shoulder joint, illustrating the anatomical region in which the invention is to be employed.

Fixation of a trackable target to the scapula presents challenges. The majority of scapular bone is thin and fragile, especially the planar body and the acromion. Attachment of a tracking device to these parts of the scapula using either a clamp or a bone screw is thus not advisable. The coracoid process (18 in FIG. 1), however, is a strong structure that is easily accessible to the surgeon during shoulder arthroplasty.

In one aspect, the invention is an anchor suitable for attaching a trackable target to the coracoid process, for tracking the scapula during shoulder replacement surgery.

Figure 2:
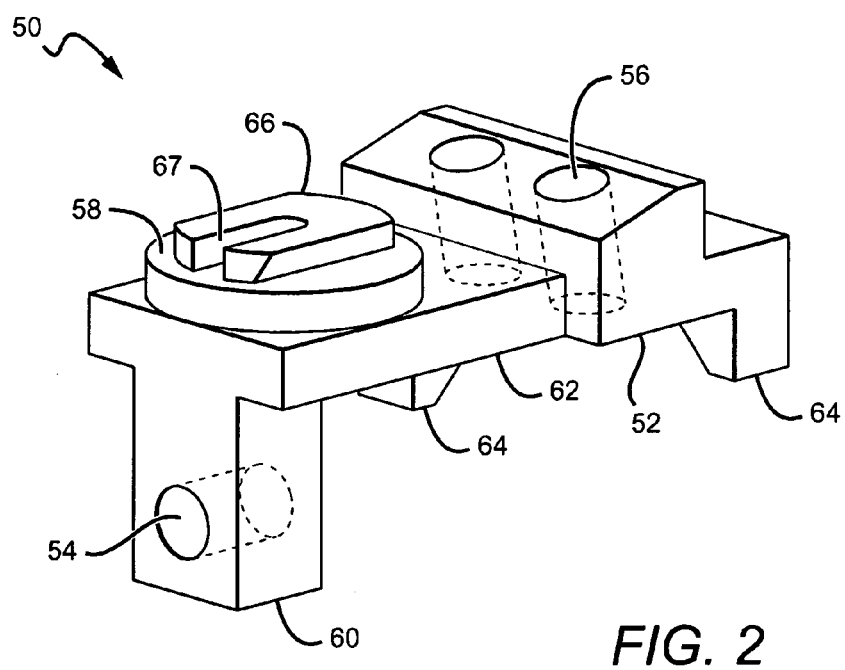
FIG. 2 is a perspective view of an anchor device in accordance with the invention, suitable for mounting a trackable target to the coracoid process of the scapula.

FIG. 2 shows an anchor in accordance with the invention, identified generally as 50. The anchor 50 includes a body 52 having at least two bores 54, 56 (and optionally more) and a coupling member 58. Body 52 is suitably L shaped, having a frontal arm 60 and a extension arm 62 as shown. One bore preferably is through the frontal arm 60 of the anchor. One or more further bores are suitably provided through the extension arm 62. Preferably, the bores are positioned in an offset or staggered manner, so that screws directed through the bores will not interfere with one another by contact, however deeply inserted into a bone.

In a preferred embodiment, at least two bores generally converge at an angle less than or equal to 90 degrees. More specifically, the axes of at least two of the bores are disposed in an angular, converging relationship such that in the case of offset (or "skew") bores, if a vector along a first bore axis is translated without rotation to a plane where it intersects the axis defined by a second bore, the intersection would define an interior angle less than or equal to 90 degrees. A consistent convention for vector direction should be observed. For example, the end where the screw head will be placed is suitable for the origin or "tail"; the direction directed into the interior of the bone (toward the sharper tip of the bone screw) may be defined as the "tip" or destination end of the vector.

The inner surface of the anchor body presents at least three prominences 64 that facilitate definite and secure engagement of the anchor with the possibly uneven surfaces of the coracoid process. The prominences may include teeth, posts, or spikes, or other such features to enhance secure engagement.

Figure 3:
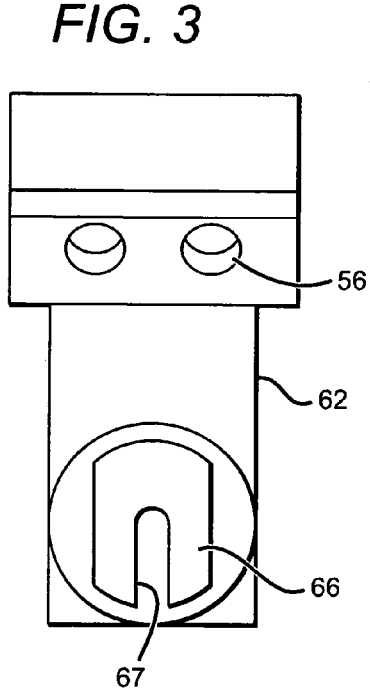
FIG. 3 is a plan view of the anchor of FIG. 2.
Figure 5:
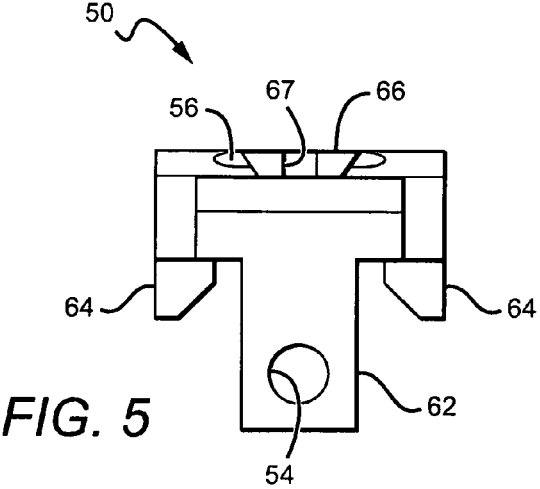
FIG. 5 is an end elevation view of the anchor of FIG. 2.
Figure 4:
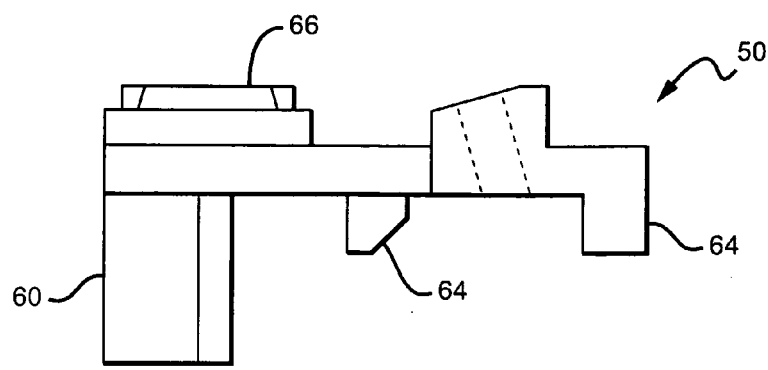
FIG. 4 is a side elevation view of the anchor of FIG. 2.

A first member 66 of a releasable coupling is either integrated with or otherwise fixed to the anchor 50. The complementary member is attached to a trackable target, and is not shown in FIG. 2. In one embodiment, the first member 66 comprises one member of a dovetailed joint, for example a tongue as shown) which extends above the top of the anchor body. The dovetail tongue 66 can also be seen in FIGS. 3-5. The dovetail is preferably cut from a partial cylinder, so that when the first member 66 is joined with its mate the resulting union will define a generally cylindrical solid. A guide slot 67 is preferably provided to help center and guide the coupling by engaging a center pin carried in the complementary member of the coupling (discussed below).

The male and female members of the dovetailed joint may equivalently be exchanged in other embodiments, so that slot is carried in the first member and tongue on second member.

FIG. 6 shows a complementary second coupling member 68 carrying an (optically) trackable marker 69. The second member has a dovetailed slot or void 70 which snugly receives and mates with the dovetail tongue 66 in the first member of the coupling. The dovetail slot 70 is preferably cut from a rotationally symmetrical piece (suitably of rigid material such as steel). Preferably, the slot is cut in a cylindrical piece; but alternatively, the members 66 and 70 could both be cut from conical volumes. Generalized, the coupling members 54 and 56 should preferably, when joined, describe a substantially solid joint which has rotational symmetry about an axis. Thus, when the coupling is mated the dovetailed tongue 66 occupies the dovetail slot 70 so that the two complementary members together comprise a substantially solid volume with rotational symmetry (for example, a cylindrical or a conical volume).

Once the coupling members 66 and 70 are mated, the mating relationship can be retained and centered by lowering a sleeve 74 to coaxially surround and center the two mated, dovetailed members. (For clarity, the sleeve 74 is shown retracted and disengaged. It should be understood that the coaxial sleeve is slidable in the axial direction within limits.) The sleeve 74 should preferably have rotational symmetry which corresponds to the exterior shape of the dovetailed joint. For example, a cylindrical sleeve 74 should have an interior dimension which slidably envelops and coaxially surrounds the two mated dovetailed members, causing them to tend toward a centered position. In one embodiment, the upper portion 76 of the sleeve 74 is suitably threaded with inside threads 78 which engage with complementary threads 80 on the lower coupling member 68). Rotating the sleeve forcibly causes the sleeve to descend and envelop the dovetailed coupling members 66 and 70. The inside cylindrical diameter of the sleeve closely but slidably fits the outside of the cylindrical volume comprising members 66 and 70 and secures their position by containing the cylindrical volume, thereby securing the coupling in a locked and centered position.

Providing rotational symmetry for the dovetailed joint and sleeve is advantageous in that it allows for ease of assembly, yet as the joint is tightened it tends to center the assembly. The coupling is thus self-centering. This produces a reliable, well centered, repeatable fit with little uncertainty ("slop") or error.

A center pin 82 can suitably be provided in the dovetailed slot 70 as shown in FIGS. 7, 8 and 9. This pin engages with a complementary slot 67 in the dovetailed tongue member 66 (previously described and shown in FIG. 5). The center pin 82 and slot 67 facilitate rapid assembly of the coupling by helping to align the dovetailed tongue with the complementary dovetailed slot.

The second coupling member is adapted to carry a trackable target 69 in a predetermined and repeatable relationship to the coupling. Optionally, an elongated stem 92 may used as shown to displace the optical components of the trackable target 69 from the coupling. In one embodiment, a plurality of distributed, reflective spheres 94 provide an easily trackable optical target. The coupling provides a convenient method of attaching, detaching, and re-attaching the target. It may occur during surgery that during certain procedures the target tends to interfere with easy access for surgical manipulations. In such cases, the trackable target 69 can be easily decoupled. When tracking is again required, the target can easily be re-attached by engaging the coupling of 66 and 70. The coupling as described above insures that the re-attachment reliably reproduces the original, pre-determined relationship between target and anchor.

The use of an anchor and detachable coupling is advantageous because it enables use of a trackable target larger than could otherwise be carried on a single bone screw. Larger, more distributed targets facilitate tracking accuracy. For example, an optically trackable target having three reflective spheres, widely separated, is preferable to a small target having three optically trackable spheres in near proximity to one another. The combination of an anchor with a detachable coupling allows larger targets to be used, but permits detachment to reduce interference with surgical access.

The invention also includes the method of tracking the scapula by attaching a trackable target to the coracoid process, tracking the target, and inferring position of the scapula based on the position and orientation of the coracoid process. The coracoid process is an integral part of the scapula bone, and thus defines the orientation of the scapula, regardless of any rigid rotation and translation.

The apparatus and method of the invention can be used in a shoulder replacement surgery as follows: The shoulder joint is first exposed. The anchor of the invention is then attached and coupled with a trackable target, and a tracking system is activated. A tracking system such as that referenced in U.S. Pat. No. 6,711,431 can suitably be used, for example.

Figure 10:
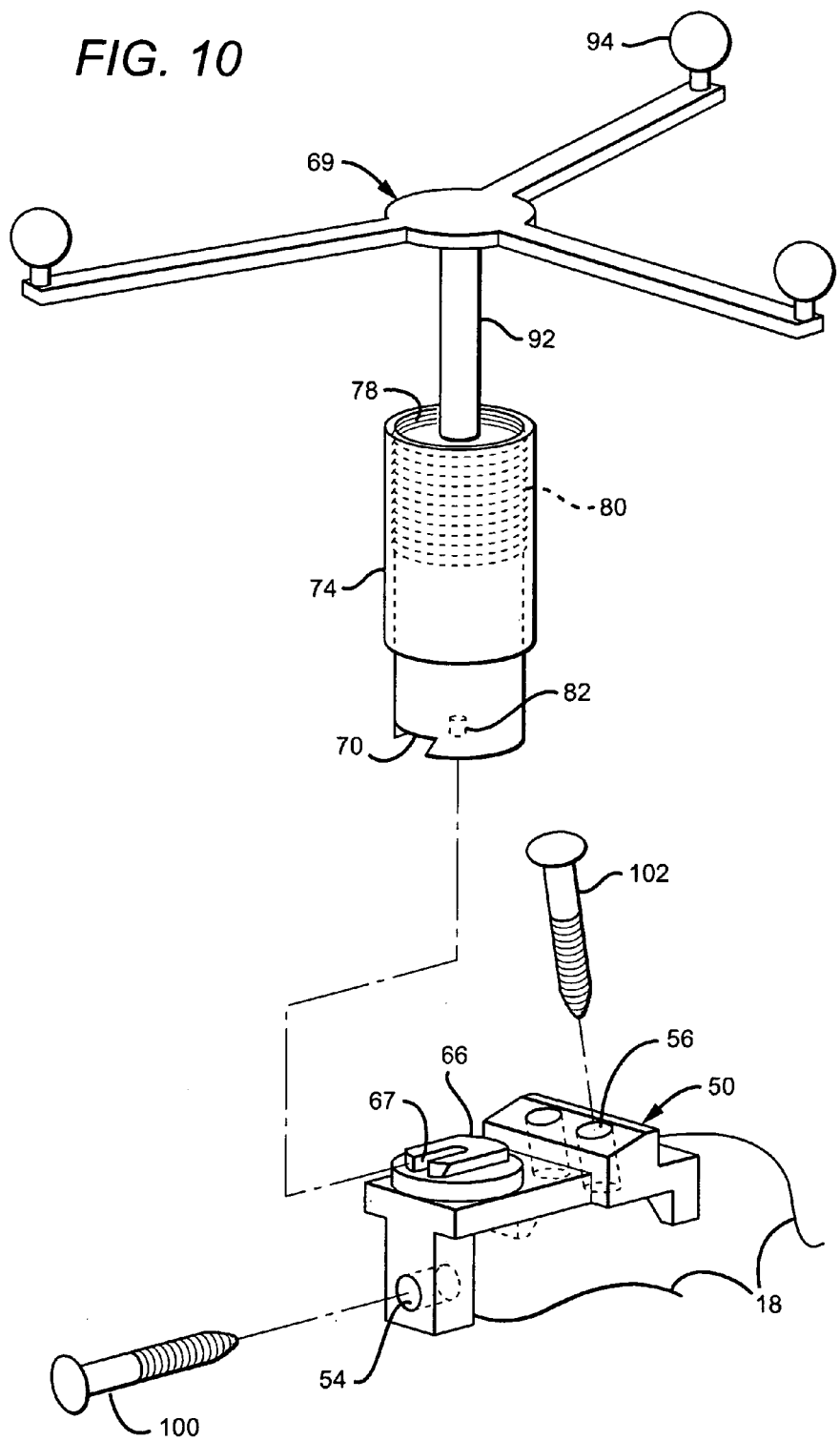
FIG. 10 is an exploded perspective view showing the anchor, mounting screws, trackable target and coupling members in relation to a coracoid process, illustrating a method of fixing the anchor and trackable target to the coracoid process to track a human scapula during shoulder replacement surgery.

The anchor of the invention may be attached to the coracoid process as follows: First, the front arm is positioned in contact with the anterior end of the coracoid process 18 as shown in FIG. 10. Next, the shaft of a self tapping surgical bone screw 100 is inserted through bore 54 and torqued, auguring the screw into the bone and clamping the arm to the end of the coracoid process 18 as the screw head is drawn toward the bone. The bone screw 100 should have a head size greater than the diameter of the bore but a shaft size which can pass through the bore. At this stage the anchor is partially fixed but still rotatable about the first bone screw 100. Next, at least one further bone screw 102 is inserted through another bore 56 and augured into the bone, tightening and fixing the anchor 50. Preferably, the first and second bores are arranged converging inward generally (but staggered or skew). As the two screws 102 and 100 are tightened the anchor is secured to the coracoid process 18. Optionally, further screws may be employed through additional bores if required. One optional additional bore is shown as an example.

After securing the anchor, the surgeon attaches a trackable target by uniting the first and second coupling members 66 and 70. The members are coupled by first sliding tongue 66 into slot 70, then lowering the sleeve 74 by rotating the sleeve. Threads 78 engage threads 80, causing the sleeve to lower, encompassing and securing the coupling members 66 and 70. The surgeon then activates a computer assisted tracking system to acquire the position of the trackable target. The tracking system thereafter acquires and accounts for any movements of the scapula. Based on the tracked movements of the scapula, the computer calculates a reference frame which is anchored to or referred to the scapula.

While the coracoid tracker is being tracked, the surgeon uses a trackable manual probe or other means to acquire the native position of significant landmarks defining the glenoid. A digital computer interfaced with the tracking system then calculates and stores the relationship between the natural glenoid and the scapular reference frame, which is updated from time to time by tracking the trackable target affixed to the coracoid. This step captures the initial geometry of the natural or "native" glenoid.

Once the initial geometry has been captured, the digital computer can recalculate from time to time the glenoid position and orientation, based on real time tracked position of the coracoid trackable target.

When the surgeon is ready to implant a glenoid component of the shoulder prosthesis, a trackable glenoid tool is used. The trackable tool could be a trackable glenoid reamer, glenoid insertion tool, or glenoid trial implant (or any combination of same). If a trackable glenoid reamer is used, the surgeon uses the reamer to prepare a glenoid cavity. During reaming, the orientation of the reamer is tracked by the tracking system. Simultaneously, the trackable target is coupled to the coracoid anchor in the field of view of the tracking system. The tracking system and digital computer then track and display the real time relationship between the glenoid tool (reamer or other tool) and the scapular reference system. Preferably, visual feedback is provided that allows comparison of the real-time glenoid geometry to the previously acquired native glenoid geometry. Any of various navigational graphic or numerical aids can be output from the digital computer to aid the surgeon in obtaining the desired orientation of the glenoid component. The reaming tool prepares a dedicated cavity for insertion of the glenoid component in an orientation defined by the (tracked) orientation of the reaming tool. Once the cavity is properly prepared, and the surgeon is satisfied with the glenoid relationship, the glenoid component is fixed to the scapula by well known surgical means (which depend on the particular prosthetic chosen).

After implantation of the prosthesis, the anchor device may be removed by removing the bone screws from the bone, freeing the device. The screws leave relatively slight damage to the coracoid process. The anchor device may then be either disposed of (in a disposable embodiment) or sterilized for re-use if fabricated from a durable material, suitable for enduring sterilization. For example, stainless steel or titanium alloys could be used.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

We claim:

1. An attachable surgical anchor, for attaching a trackable target in fixed relation to a human scapula during surgery, comprising:
   at least two bone screws;
   a body having a size and shape configured to engage a human coracoid process, said body having at least two bores for receiving the shafts of said bone screws, such that, when said body is properly positioned against a coracoid process to which said anchor is to be attached, said bores are positioned to direct said bone screws into said coracoid process thereby securing said body to the coracoid process, said body arranged such that at least two of said bores cannot move with respect to each other and are arranged at an angle relative to each other of greater than 0°;
   a coupling member, carried by said body and arranged to engage a complementary coupling member bearing an optically trackable target comprising a plurality of distributed, reflective markers which define a plane; and
   a complementary coupling member bearing a trackable target and which is arranged to engage said coupling member, such that said body and coupling member serve as a surgical anchor when attached to said coracoid process, said complementary coupling member and said trackable target being separate and distinct from said bores and said bone screws.

2. The surgical anchor of claim 1, wherein said at least two bores have axes arranged in a staggered configuration to prevent interference between said bone screws.

3. The surgical anchor of claim 1, wherein said body has at least three prominences adapted to contact the surface of said coracoid process, said prominences arranged to ensure that said body is properly positioned against said coracoid process and to thereby facilitate secure engagement of said anchor to said coracoid process surface when said anchor is secured to said coracoid process.

4. The surgical anchor of claim 1, wherein said coupling member is adapted to engage with said complementary member in a predetermined and repeatable relationship.

5. The surgical anchor of claim 1, wherein said coupling member comprises a member of a dovetailed joint.

6. The surgical anchor of claim 1, wherein said coupling member is adapted to mate with said complementary coupling member in a self centering position.

7. The surgical anchor of claim 1, wherein said coupling is constrained to mate in a position having a definite geometric relationship to its complementary member.

8. The surgical anchor of claim 1, wherein said at least two bores arranged at an angle relative to each other of greater than 0° are further arranged to converge at an angle relative to each other that is less than or equal to 90°.

9. The surgical anchor of claim 1, wherein said body comprises a first arm and a second arm arranged at an angle relative to each other of greater than 0°, at least one of said at least two bores arranged at an angle relative to each other of greater than 0° provided through each of said first and second arms.

10. The surgical anchor of claim 9, wherein said body is generally L shaped.

11. The surgical anchor of claim 1, wherein said coracoid process has an associated anterior end and an upper surface, said anchor arranged such that bone screws directed into said coracoid process via said at least two bores arranged at an angle relative to each other of greater than 0° secure said body to both the anterior end and the upper surface of said coracoid process.

12. An attachable surgical anchor, for attaching a trackable target in fixed relation to a human scapula during surgery, comprising:
    at least two bone screws;
    an L-shaped body having a size and shape configured to engage a human coracoid process, said body comprising a first arm and a second arm arranged at an angle relative to each other of greater than 0°;
    at least one bore through each of said first and second arms for receiving the shafts of said bone screws, said body arranged such that said bores through each of said first and second arms cannot move with respect to each other and are arranged to converge at an angle relative to each other that is greater than 0° and less than or equal to 90°, such that bone screws directed into said coracoid process via said bores through each of said first and second arms secure said body to both the anterior end and the upper surface of said coracoid process;
    a coupling member, carried by said body and arranged to engage a complementary coupling member bearing a trackable target; and
    a complementary coupling member bearing an optically trackable target comprising a plurality of distributed, reflective markers which define a plane and which is arranged to engage said coupling member, such that said body and coupling member serve as a surgical anchor when attached to said coracoid process, said complementary coupling member and said trackable target being separate and distinct from said bores and said bone screws.

13. The surgical anchor of claim 1, wherein said at least two of said bores which cannot move with respect to each other and are arranged at an angle relative to each other of greater than 0° lie in respective planes which are parallel to each other.

14. The surgical anchor of claim 12, wherein said body includes at least three prominences arranged to facilitate the secure engagement of said anchor with said coracoid process.

* * * * *